(12) United States Patent
Wood

(10) Patent No.: US 6,478,026 B1
(45) Date of Patent: Nov. 12, 2002

(54) NASAL VENTILATION INTERFACE

(76) Inventor: Thomas J. Wood, 1909 Tebeau St., Waycross, GA (US) 31501

( * ) Notice: Subject to any disclaimer, the term of this patent is extended or adjusted under 35 U.S.C. 154(b) by 0 days.

(21) Appl. No.: 09/524,371

(22) Filed: Mar. 13, 2000

Related U.S. Application Data

(60) Provisional application No. 60/124,323, filed on Mar. 13, 1999.

(51) Int. Cl.$^7$ .............................................. A61M 15/08
(52) U.S. Cl. .............................. 128/207.18; 128/207.13
(58) Field of Search ........................ 128/207.18, 207.13, 128/207.12, 203.29, 204.12, 204.26, 205.27, 205.29, 206.11, 206.15, 206.18; 600/529, 538, 532

(56) References Cited

U.S. PATENT DOCUMENTS

| | | | | | |
|---|---|---|---|---|---|
| 1,125,542 | A | * | 1/1915 | Humphries | 128/207.18 |
| 3,670,726 | A | | 6/1972 | Mahon et al. | 128/188 |
| 3,739,774 | A | | 6/1973 | Gregory | 128/142.7 |
| 3,861,385 | A | | 1/1975 | Carden | 128/145.8 |
| 3,902,486 | A | | 9/1975 | Guichard | 128/140 N |
| 3,905,361 | A | | 9/1975 | Hewson et al. | 128/145.5 |
| 4,106,505 | A | * | 8/1978 | Salter et al. | 128/207.18 |
| 4,267,845 | A | | 5/1981 | Robertson, Jr. et al. | 128/721 |
| 4,312,359 | A | | 1/1982 | Olson | 128/680 |
| 4,367,735 | A | | 1/1983 | Dali | 128/207.18 |
| 4,406,283 | A | | 9/1983 | Bir | 128/207.18 |
| 4,422,456 | A | * | 12/1983 | Tiep | 128/207.18 |
| 4,493,614 | A | | 1/1985 | Chu et al. | 417/22 |
| 4,549,542 | A | | 10/1985 | Chien | 128/201.24 |
| 4,587,967 | A | | 5/1986 | Chu et al. | 128/204.21 |
| 4,601,465 | A | | 7/1986 | Roy | 272/99 |
| 4,617,637 | A | | 10/1986 | Chu et al. | 364/505 |
| 4,699,139 | A | * | 10/1987 | Marshall et al. | 128/207.18 |
| 4,706,664 | A | | 11/1987 | Snook et al. | 128/204.23 |
| 4,753,233 | A | * | 6/1988 | Grimes | 128/207.18 |

(List continued on next page.)

FOREIGN PATENT DOCUMENTS

| | | | | | |
|---|---|---|---|---|---|
| DE | DL 146688 | * | 2/1981 | | 128/207.18 |
| GB | 0532214 | | 1/1941 | | |
| WO | WO-90/01963 | * | 3/1990 | | 128/207.18 |

*Primary Examiner*—John G. Weiss
*Assistant Examiner*—Teena Mitchell
(74) *Attorney, Agent, or Firm*—Richard C. Litman

(57) ABSTRACT

A nasal ventilation interface comprising a hollow body having at least one and preferably two nasal apertures, and at least one and preferably two inhale apertures, and at least one and preferably two nasal insert tubes each associated with one of the nasal apertures and having an annular sleeve that forms a seal with a nostril of the patient. The hollow body has at least one and preferably two exhale apertures and at least one valve assembly associated with the exhale apertures that is capable of preventing air from passing through the exhale aperture upon the patient inhaling and allowing air to pass through the exhale aperture upon exhaling. The hollow body may also have at least one and preferably two filters for retaining heat and moisture from the exhale air and transferring the retained heat and moisture into the inhale air.

10 Claims, 8 Drawing Sheets

U.S. PATENT DOCUMENTS

| | | | |
|---|---|---|---|
| 4,774,946 A | 10/1988 | Ackerman et al. | 128/207.18 |
| 4,793,343 A | 12/1988 | Cummins, Jr. et al. | 128/204.17 |
| 4,840,169 A | 6/1989 | Folsom | 128/863 |
| 4,850,346 A | 7/1989 | Michel et al. | 128/206.15 |
| 4,899,740 A | 2/1990 | Napolitano | 128/202.22 |
| 4,915,105 A * | 4/1990 | Lee | 128/205.27 |
| 4,967,742 A | 11/1990 | Theodorou | 128/202.13 |
| 5,000,173 A | 3/1991 | Zalkin et al. | 128/204.21 |
| 5,011,474 A | 4/1991 | Brennan | 604/54 |
| 5,022,900 A | 6/1991 | Bar-Yona et al. | 55/316 |
| 5,025,805 A * | 6/1991 | Nutter | 128/207.18 |
| 5,038,772 A | 8/1991 | Kolbe et al. | 128/205.41 |
| 5,074,297 A | 12/1991 | Venegas | 128/204.18 |
| 5,113,857 A * | 5/1992 | Dickerman et al. | 128/207.18 |
| 5,121,745 A | 6/1992 | Israel | 128/202.28 |
| 5,127,397 A | 7/1992 | Kohnke | 128/202.28 |
| 5,137,017 A * | 8/1992 | Salter | 128/207.18 |
| D333,015 S | 2/1993 | Farmer et al. | D29/8 |
| 5,188,101 A | 2/1993 | Tumolo | 128/207.18 |
| 5,265,592 A | 11/1993 | Beaussant | 128/201.24 |
| 5,265,595 A | 11/1993 | Rudolph | 128/204.18 |
| 5,271,391 A | 12/1993 | Graves | 128/207.18 |
| 5,299,599 A | 4/1994 | Farmer et al. | 137/625.22 |
| 5,335,656 A * | 8/1994 | Bowe et al. | 128/207.18 |
| 5,372,130 A | 12/1994 | Stern et al. | 128/205.25 |
| 5,375,593 A | 12/1994 | Press | 128/207.18 |
| 5,385,141 A | 1/1995 | Granatiero | 128/201.19 |
| 5,394,568 A | 3/1995 | Brostrom et al. | 2/452 |
| 5,396,885 A | 3/1995 | Nelson | 128/204.18 |
| 5,398,676 A | 3/1995 | Press et al. | 128/204.23 |
| 5,400,776 A * | 3/1995 | Bartholomew | 128/200.24 |
| 5,425,359 A * | 6/1995 | Liou | 128/206.11 |
| 5,437,267 A * | 8/1995 | Weinstein et al. | 128/200.23 |
| 5,509,409 A * | 4/1996 | Weatherholt | 128/207.18 |
| 5,526,806 A | 6/1996 | Sansoni | 128/207.18 |
| 5,533,506 A | 7/1996 | Wood | 128/207.18 |
| 5,682,881 A * | 11/1997 | Winthrop et al. | 128/207.18 |
| 5,740,799 A | 4/1998 | Nielsen | 128/207.18 |
| 5,794,619 A * | 8/1998 | Edelman et al. | 128/207.18 |
| 5,906,203 A * | 5/1999 | Klockseth et al. | 128/205.24 |

* cited by examiner

NASAL VENTILATION INTERFACE

This application claims priority from provisional application Ser. No. 60/124,323, filed Mar. 13, 1999.

FIELD OF THE INVENTION

The present invention relates generally to nasal ventilation systems, and more particularly, to a valved nasal ventilation interface for supporting respiration.

BRIEF DESCRIPTION OF THE PRIOR ART

Nasal ventilators generally consist of tubes and other means for delivering gases adapted for use with the nasal or oral passage of a patient. Typically, a nasal ventilation system comprises a gas source and a mechanical ventilator such as a continuous positive airway pressure system (CPAP), bi-level positive airway pressure system (BIPAP), or intermittent (non-continuous) positive pressure (IPPB). The gas is often room air or oxygen-enriched air, but can be a mixture of other gases.

The gas is transported by a thin flexible tube made of an inert material. The tube terminates in an opening which can be inserted into the patient's nostrils. Typically, a pair of smaller nasal insert tubes protrude from the tube or the tube splits at a Y-junction into two smaller tubes, each smaller nasal insert tube carrying gas to one nostril, thereby increasing the fraction of inspired oxygen.

Conventional nasal tube systems do not provide a positive seal between the nasal insert tubes and the nostrils. Most nasal ventilation systems therefore include a mask that fits over the nose and is intended to provide a space of oxygen-enriched air for inhalation into the lungs for respiration. Such systems frequently suffer from air leaking out around the mask, creating an inability to assure ventilation in many patients.

For example, conventional nasal ventilation systems use head gear and/or straps to bind the mask in place, but in order to minimize the leakage of the air the straps must be sufficiently tight. The mask, headgear, and/or straps thereby exert more than a minor pressure on the patient's face and/or head, resulting in such masks and headgear tending to be rather constraining and uncomfortable.

Additionally, most systems are usually very position dependent, whereby if the mask is moved slightly with respect to the facial contour or with respect to the nose, air leakage occurs. With such systems, the mask can become uncomfortable when not in position, thus requiring the patient to remain rather still in order to alleviate the discomfort and to maintain oxygen inspiration. As a result many patients lose interest in using the nasal mask.

Also, some ventilation systems have exhalation valves for the treatment of breathing problems. Various valve systems have been devised but they all function similarly. Typically, the exhalation valve is positioned at the ventilator or in the tubing at least a foot or more from the patient, and the air that is exhaled by the user is trapped in this "dead space" between the patient and the valve. Such ventilation systems with exhale valves are typically bulky and heavy. The patient thus has to have a tidal volume (breath) that is a little larger than otherwise needed to compensate for the deadspace. This larger tidal volume is noticeable by the patient and can be a nuisance while trying to sleep soundly.

Related types of nasal tube systems include low flow oxygen systems which merely provide oxygen concentration. These systems typically provide nasal insert tubes that are loosely inserted into the nasal cavities without a mask. Such systems are low pressure systems for providing oxygen enrichment to the ambient air that the patient breathes, are not ventilators (do not provide positive pressure for forced ventilation/breathing), and could not function as ventilation systems because of the lack of a seal between the cannula interface and the patient, the smaller tubing size, and the low pressure of the system.

Additionally, there are no known portable, wearable devices that completely filter out the allergens that trigger allergic reactions in asthmatics and allergy sufferers. There are only aerosol treatments and other medications that treat the symptoms, that is, the allergic reactions themselves. Furthermore, when a patient presents to an emergency room with severe bronchial constriction in response to allergens, a bronchodilator is typically administered to dilate the tracheal airways and bronchioles so that gas exchange is maintained in the alveoli of the lungs. However, if bronchial dilation is successful then allergens are also allowed to be breathed deeper into the bronchioles. Bronchiole constriction is a bodily reaction to keep any further allergens from reaching the smaller airways. Forced dilation and deeper penetration of allergens often results in an even more violent reaction after the bronchodilator has lost some of its therapeutic effect. This worsened reaction sometimes becomes life-threatening and can cause death, in particular, to a patient with status asthmaticus.

Furthermore, present cloth surgical masks typically worn by doctors, surgeons, and other medical personnel do not filter out many pathogens. Also, they are hot to the wearer and can obstruct the wearer's view, especially when looking down during a surgical procedure. Dentists are concerned with spray and do not trust the presently available surgical masks.

Accordingly, what is needed but not found in the prior art is a nasal interface apparatus that can be used with a positive pressure ventilation system for supporting respiration, that directs substantially all the air delivered to the nasal interface into the patient's lungs, that is comfortable and unconstraining to the patient wearer.

SUMMARY OF THE INVENTION

Generally described, the present invention provides a nasal ventilation interface comprising a hollow body having at least one and preferably two nasal apertures, at least one and preferably two inhale apertures, at least one and preferably two connectors each capable of being removably attached to at least one of preferably two interface tubes, and at least one and preferably two nasal insert tubes each associated with one of the nasal apertures of the body and capable of being inserted into a nostril of a patient. Each nasal insert tube has an annular sleeve with a contact surface and a diameter that is greater than a diameter of the nasal insert tube so that each annular sleeve contact surface is thereby capable of forming a seal with the nostril. The nasal insert tube may be detachably coupled to the hollow body. There may also be provided a three-way junction capable of being removably connected to a feed tube.

The hollow body may have at least one exhale aperture and at least one valve assembly associated with the exhale aperture that is capable of preventing air from passing through the exhale aperture upon the patient inhaling and allowing air to pass through the exhale aperture upon exhaling. The hollow body may also have at least one filter that retains heat and/or moisture from air passing therethrough upon inhalation and that transfers the heat and/or moisture to the exhalation air that subsequently passes therethrough upon exhalation.

In a first embodiment of the present invention, each valve assembly comprises a valve member pivotally attached to a first inner wall of the and a second valve member pivotally attached to a second inner wall of the body opposite the first inner wall. The first and second valve members overlap and abut each other so that each valve member may pivot in response to the other valve pivoting. In a second embodiment of the present invention, each valve assembly comprises a one-way inhale valve membrane arranged in the body between the nasal aperture and the exhale aperture or disposed within the inhale aperture, and a one-way exhale valve membrane disposed within the exhale aperture. In a third embodiment of the present invention, the body is provided for use without the gas supply, mechanical ventilator, or tubing, valving may or may not be provided, and a filter is provided for screening out dust, allergens, pollen, bacteria, viruses, pathogens, and other air-borne particle matter, so that the invention may be used as a portable nasal filtration device.

Accordingly, it is an object of the present invention to provide a positive pressure closed system providing for full ventilation of a patient with oxygen enrichment capabilities typically provided by low pressure oxygen concentrator and cannula tubing systems.

It is another object of the present invention to provide a nasal ventilation interface having improved patient comfort for use over extended periods.

It is a further object of the present invention to provide a nasal ventilation interface having increased gas delivery efficiency and with minimal or no leakage of gas from the nostrils.

It is still another object of the present invention to provide a nasal ventilation interface having automatic valving for inhaling and exhaling.

It is yet another object of the present invention to provide a nasal ventilation interface with a valve assembly that decreases the amount of deadspace that is rebreathed by the patient.

It is yet a further object of the present invention to provide a nasal ventilation interface that filters the air that is inhaled and/or exhaled for heat, moisture, allergens, pollen, bacteria, viruses, pathogens, and other air-borne particle matter.

These and other objects, features, and advantages of the present invention are discussed or apparent in the following detailed description of the invention, in conjunction with the accompanying drawings and the appended claims.

BRIEF DESCRIPTION OF THE DRAWINGS

The various features and advantages of the invention will be apparent from the attached drawings, in which like reference characters designate the same or similar parts throughout the figures, and in which.

DETAILED DESCRIPTION OF THE PREFERRED EMBODIMENTS

Figure 1:
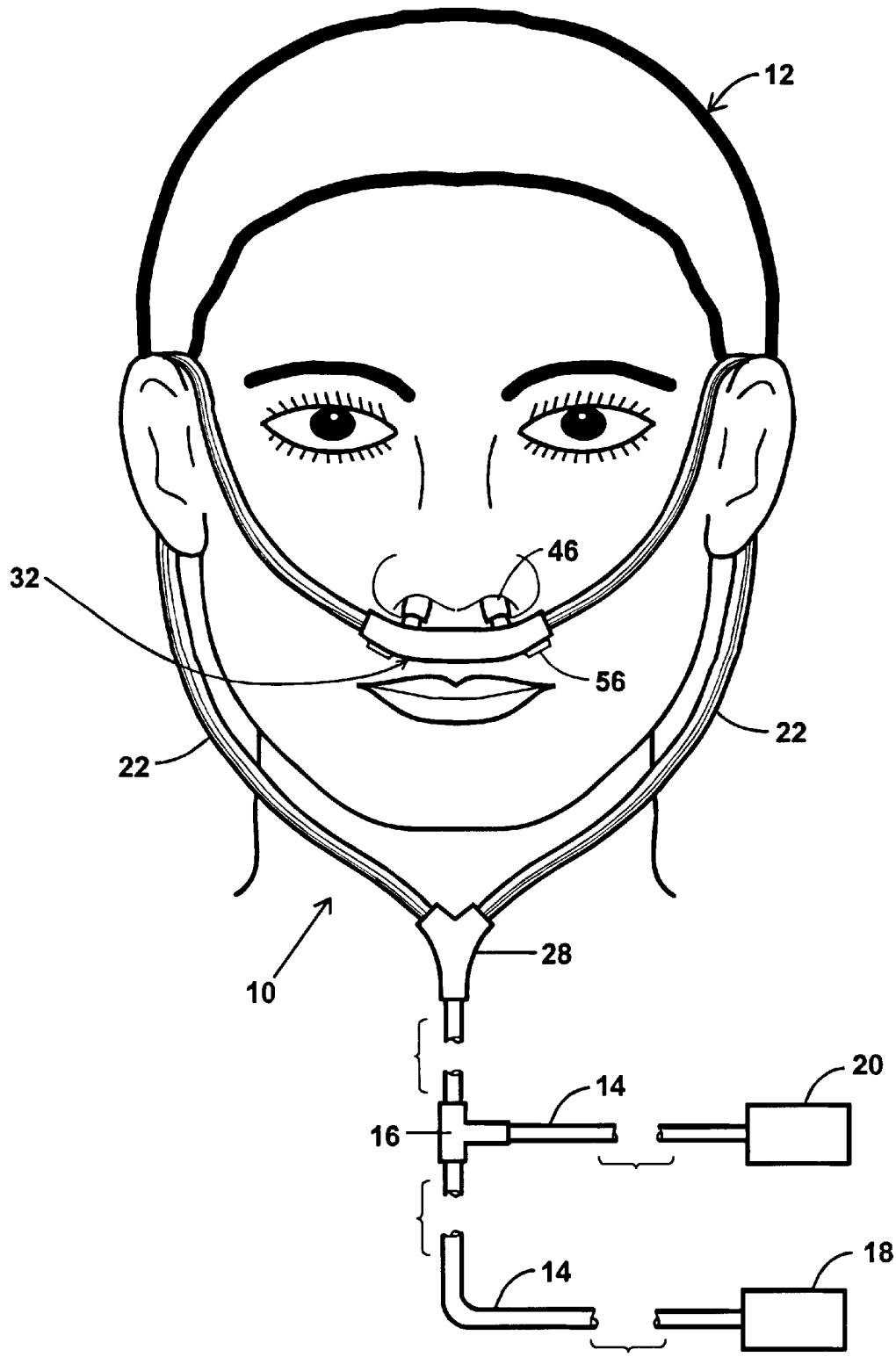
FIG. 1 is a side elevation view of a first preferred embodiment of the present invention in use by a patient.

Referring now to FIG. 1, there is illustrated a first embodiment 10 of the present nasal interface invention as typically worn by a patient 12. The interface 10 may be connected by feed tubing 14 and a feed valve 16 to a mechanical ventilator 18 and a gas supply 20. The feed tubing 14 may be a thin flexible tube made of an inert material such as polyurethane, silicone, or another material known in the art. It will be noted that all components of the interface 10 may be made of medical grade biocompatible materials.

The mechanical ventilator 18 forces a gas such as air through the tubing 14. The mechanical ventilator 18 may be provided by a continuous positive airway pressure (CPAP) machine for constant air pressure delivered through the interface 10 to the patient 12. Alternatively, the mechanical ventilator 18 may be provided by a bilateral positive airway pressure (BIPAP) machine for intermittent air pressure delivered through the interface 10 to the patient 12, whereby the pressure is lower during exhale than during inhale to facilitate breathing by the patient 12. Other mechanical ventilators known by those skilled in the art may be suitable, such as IPPB mechanical ventilators. A power source and controls (not shown) are provided for operating the mechanical ventilator 18.

The gas supply 20 may be a tank of oxygen or another gas as may be appropriate in a given situation. The oxygen may be mixed with air to form oxygen-enriched air, with the oxygen concentration controlled by the valve 16. It will be understood that other gases or mists can be provided as may be desired in a given application.

Figure 2:
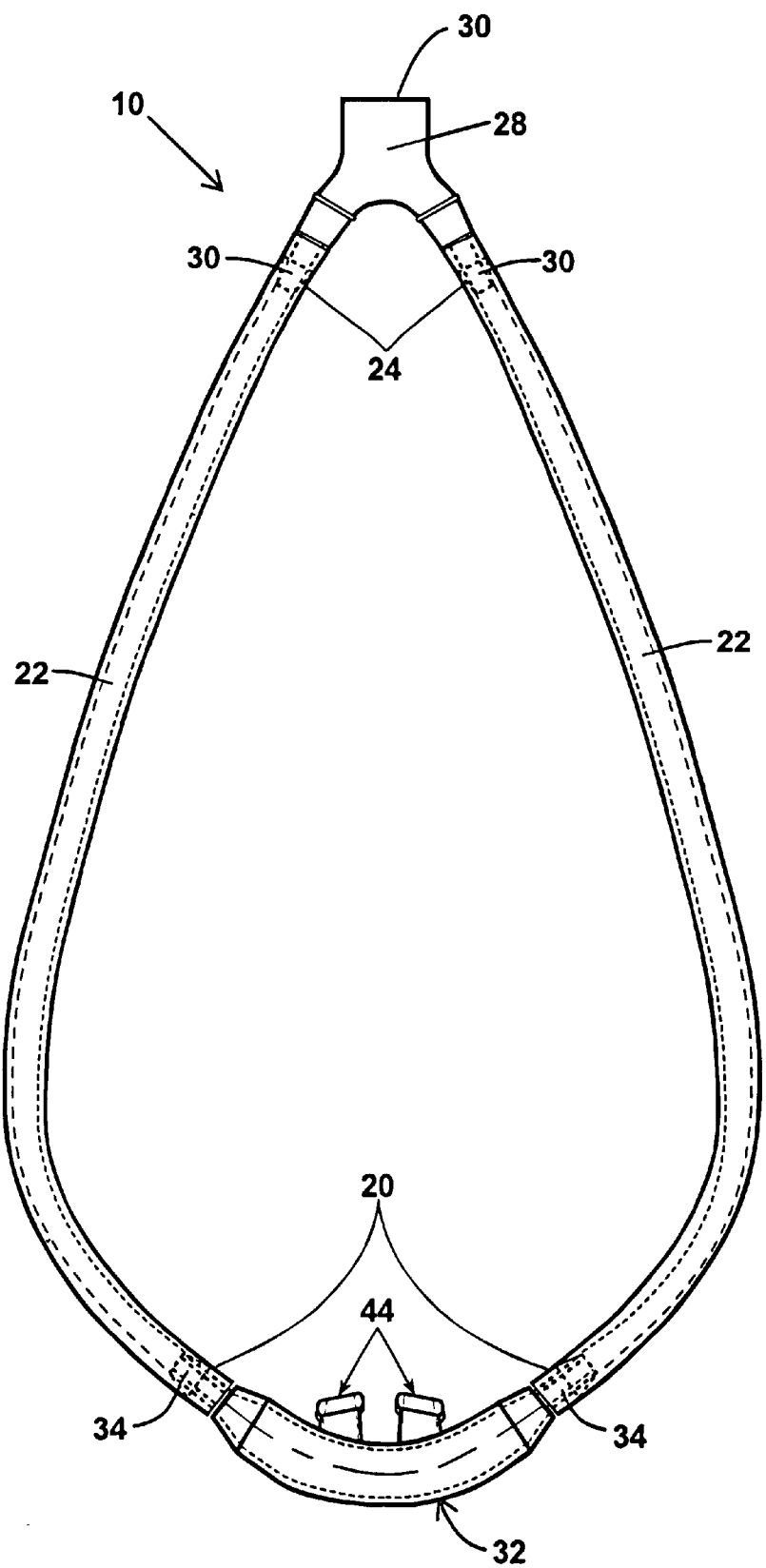
FIG. 2 is a plan view of the embodiment of FIG. 1.

Referring now to FIGS. 1 and 2, there may be provided two lengths of interface tube 22 each having a first end 24 and a second end 26, a three-way tubing junction 28 with two connectors 30 each capable of being removably attached to one of the first ends 24 of the tube 22, and a hollow body 32 with two tubing connectors 34 each capable of being removably attached to one of the second ends of the tube 22.

The three-way tubing junction 28 may be provided by a "Y" junction, a "T" junction, or another junction as is known in the art, with the connectors 30 of a type known in the art for connecting tubing.

The tube 22 may be a thin flexible tube made of an inert material such as polyurethane, silicone, or another material known in the art. The tubes 22 may be of a smaller size than tube 14 where two tubes 22 carry the same volume of gas as the one tube 14. The feed tube 22 size is selected to provide a sufficient air volume flow therethrough for full ventilation of the patient 12. For example, the size of the feed tube 22 may be selected to accommodate about 120 liters per minute of air therethrough. On the other hand, typical low pressure oxygen cannula tubing is sized to accommodate about 5 liters per minute.

Figure 4:
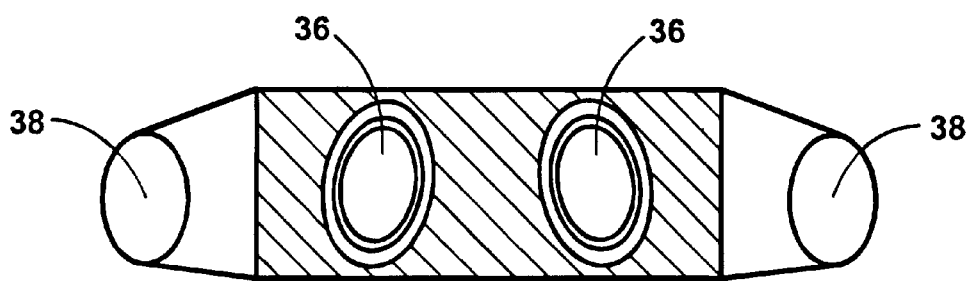
FIG. 4 is a top plan view of FIG. 3.
Figure 3:
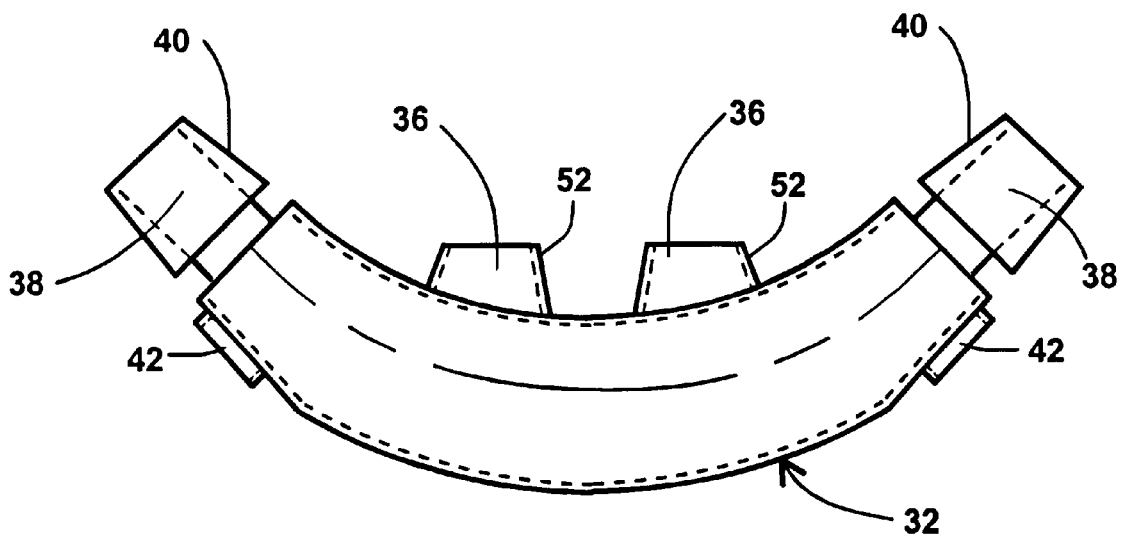
FIG. 3 is a side elevation view of the hollow body of the embodiment of FIG. 1.

Referring now to FIGS. 3 and 4, the hollow body 32 has at least one and preferably two nasal apertures 36 defined therein, at least one and preferably two inhale apertures 38 defined therein, at least one and preferably two connectors 40 associated with each inhale aperture 38 and capable of being removably attached to said second ends of said interface tubing 22, and at least one exhale aperture 42 defined therein. The body 32 may be made of a polycarbonate, plastic, polymer, metal, ceramic, composite, or other material known in the art. The body 32 may have a generally cylindrical, rectangular, or other regular or irregular shape. The connectors 30 are of a type known in the art for connecting tubing.

Figure 5:
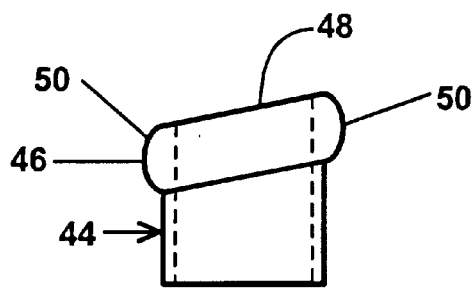
FIG. 5 is a side elevation view of the nasal insert tube of the embodiment of FIG. 1.
Figure 6:
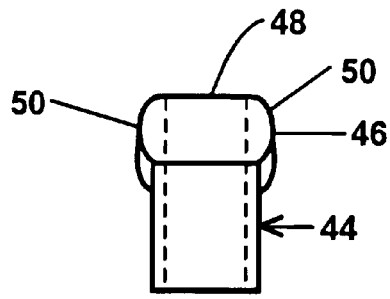
FIG. 6 is a front elevation view of the nasal insert tube of the embodiment of FIG. 1.

Referring now to FIGS. 5 and 6, there is provided at least one and preferably two nasal insert tubes 44 each capable of being inserted into a nostril of the patient 12. Each nasal insert tube 44 has at least one annular sleeve 46 with a surface 50 formed thereon for forming a gentle but firm seal with the inner wall of one of the patient's nostrils. The annular sleeves 46 may be made of a soft pliable material for patient comfort such as a silicone elastomer or another material known in the art for providing a surface for forming the gentle but firm seal between the sleeve 46 and the patient's skin. The annular sleeves 46 preferably have a generally oval shape for conforming to the shape of the patient's nostrils to form the seal as described herein, however, other regular or irregular shapes may be provided.

In order to secure the interface 10 in place without the need for headgear and/or straps, a force is generated by the sleeves 46 on the inner walls of the each nostril. This is accomplished by providing each sleeve 46 with a diameter that is greater than a diameter of the corresponding nasal insert tube 44. The contact surface 50 thereby provides a surface area sufficient to spread the required securement force over sufficiently large area of the inner walls of the nostrils for improved patient comfort. Additionally, the lobes of most patient's nostrils are generally angled, and each annular sleeve 46 may have an angled end 48 conforming thereto for allowing the annular sleeves 46 to be inserted into the patient's nostrils no more than is necessary to form the seal.

Each nasal insert tube 44 may be detachably coupled to the hollow body 32 so that the interface may be reused by merely changing out the sleeves 44 for each new use. This may be beneficial in certain applications, for example, for hospital or other uses. Where the interface is provided with detachable nasal insert tubes 44, the body may be provided with at least one and preferably two hollow members 52 extending from the body 32 (see FIGS. 3 and 4), each hollow member capable of detachably receiving one of the nasal insert tubes 44. The hollow members 52 may have a shape that is frusto-conical which provides a smooth transition of airflow from the body 32 into the nasal insert tubes 44. Alternatively, the hollow members may have a cylindrical or other regular or irregular shape.

Alternatively, the nasal insert tubes 44 may be integrally formed with the body 32, an arrangement which may be beneficial in home use of the interface 10 where only one patient uses the interface 10. For such applications, the nasal insert tubes 44 may extend directly from the body 32 without the need for the hollow members 52.

Referring now to FIGS. 7–10, there is provided at least one and preferably two exhale apertures 54 defined in the body 32 and at least one valve assembly 56 associated with and preferably arranged within the body 32. The valve assembly 56 prevents inhalation air 57 from passing through the exhale aperture 54 when the patient inhales and allows exhale air 59 to pass through the exhale aperture 54 when the patient exhales. One of the exhale apertures 54 is arranged between one of the inhale apertures 38 and one of the nasal apertures 36, and one of the valve assemblies 56 is arranged between one of the inhale apertures 38 and one of the nasal apertures 36.

The valve assembly 56 may comprise a first valve member 58 having a first end 60 and having a second end 62 pivotally attached to a first inner wall 64 of the body 32 between the nasal aperture 36 and the exhale aperture 54. The valve assembly 56 may further comprise a second valve member 66 having a first end 68 and having a second end 70 pivotally attached to a second inner wall 72 of the body 32 opposite the first inner wall 64 and between the exhale aperture 54 and the inhale aperture 38. The first valve member second end 60 and the second valve member second end 68 are capable of overlapping and abutting each other so that the valve members 60 and 68 may pivot in response to each other thereby providing for controlling the airflow through the body 32 as described herein.

Figures 8, 9:
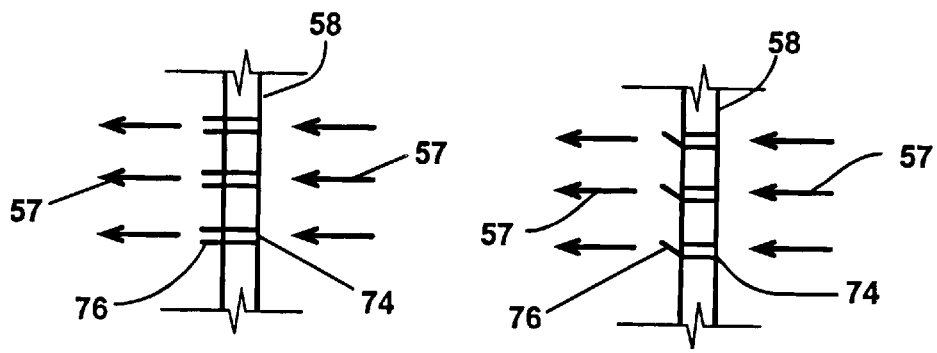
FIG. 8 is a side elevation view of the first valve member of the embodiment of FIG. 1 in a first position.
FIG. 9 is a side elevation view of an alternative first valve member of the embodiment of FIG. 1.

The first valve member 58 is made of a material providing for one-way fluid flow therethrough. As shown in FIGS. 8 and 9, for example, the first valve member may have at least one perforation 74 defined therein with at least one biased closure member 76 associated therewith such that the inhale air 57 may pass through the perforation 74 in one direction only. For example, there may be provided one biased closure member 76 for each perforation 74 (see FIG. 8), two biased closure members 76 for each perforation 74 (see FIG. 9), or other similar arrangements known in the art. Also, the biased closure member 76 may have a generally frusto-conical shape whereby air may pass through the perforation 74 from the larger conical end through the smaller conical end, but not vice versa. The first valve member 60 may be made of a plastic, polymer, metal, composite, or other material known in the art. The second valve member 66 is non-perforated and may be made of a solid plastic, polymer, metal, composite, or other material known in the art.

Figure 7:
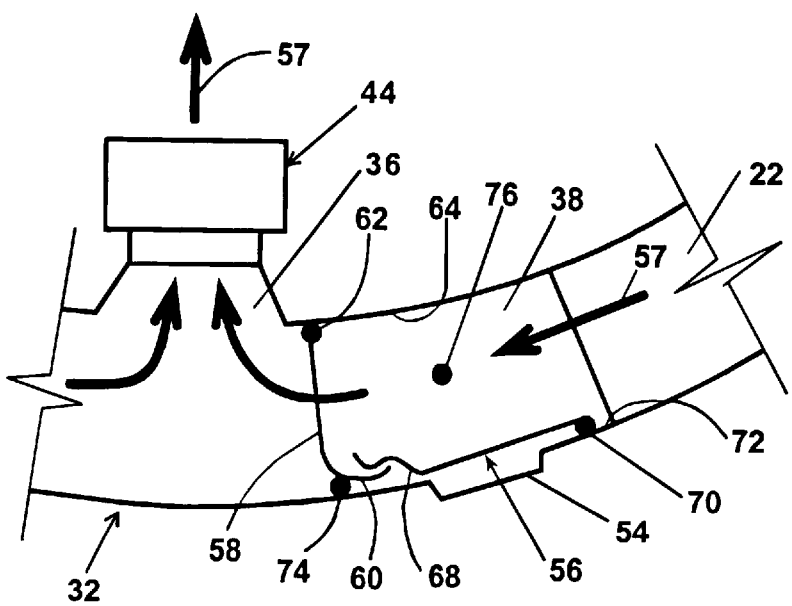
FIG. 7 is a side elevation view of the embodiment of FIG. 1.

FIG. 7 shows the second valve member 66 pivoted to a first position where the second valve member 66 substantially covers the exhale aperture 54 in response to a force thereon from the patient 12 inhaling air 57 through the inhale aperture 38. In this first position, the exhale aperture 54 is substantially covered by the second valve member 66 alone, by a combination of the second valve member 66 and the first valve member 58, or by a combination of the second valve member 66, the first valve member 58, and a stop that will be described hereinafter. The first valve member 58 pivots to a first position in response to the pivoting of the second valve member 66 as a result of the second end 68 of the second valve member 60 contacting and forceably moving the second end 60 of the first valve member 58. The first valve member 58 is thereby suitably positioned to receive a force from the exhale air 59 as will described immediately hereinafter.

Figure 10:
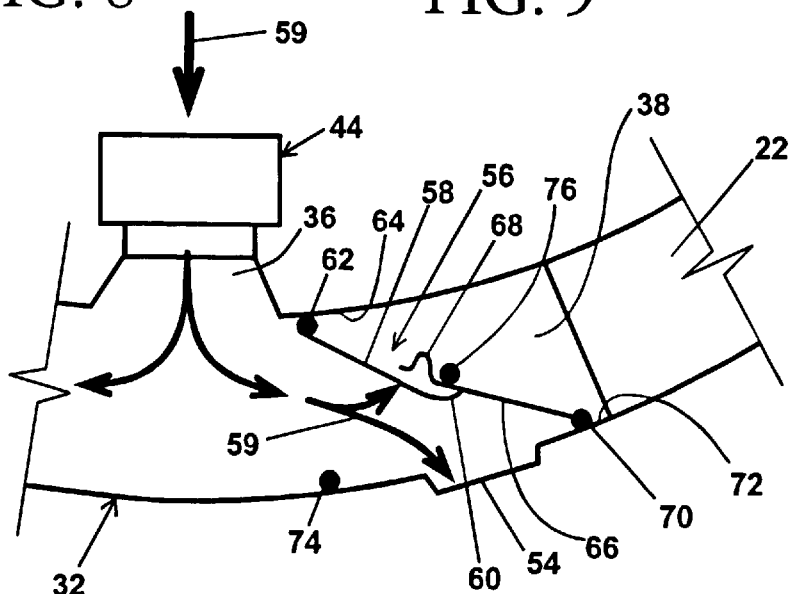
FIG. 10 is a side elevation view of the first valve member of the embodiment of FIG. 1 in a second position.

FIG. 10 shows the first valve member 58 pivoted to a second position in response to a force thereon from the patient 12 exhaling air 59 through the nasal aperture 36. When the first valve member 58 pivots to the second position, the first valve member second end 60 contacts the second valve member second end 68 and forces the second valve member 66 to a second position. In this second position, the exhale aperture 54 is not covered so that the exhale air 59 may pass through the exhale aperture 54.

In order to limit the range of pivotal motion of the valve members 58 and 66 and thereby maintain their second ends 60 and 68 in abutting contact, there may be provided at least one and preferably two stops 74 and 76 arranged within the body 32. The first stop 74 limits the pivoting motion of the first valve member 58 to the first position and the second stop 76 limits the pivoting motion of the second valve member 66 to the second position. The stops 74 and 76 may be provided by rods, bars, tabs, arms, or the like extending across or into the body 32.

Alternatively to or in combination with the stops 74 and 76, the range of pivotal motion of the valve members 58 and 66 may be accomplished by the second end 60 of the first valve member 58 having an angled portion and the second end 68 of the second valve member 66 having a yoke or the like defined thereon that receives the angled second end 60 when the valve members 58 and 66 are pivoted to the first positions. In another alternative, the second end 68 of the second valve member 66 has an angled portion and the second end 60 of the first valve member 58 has a yoke or the like defined thereon that receives the angled second end 66 when the valve members are pivoted to the first positions.

Figure 11:
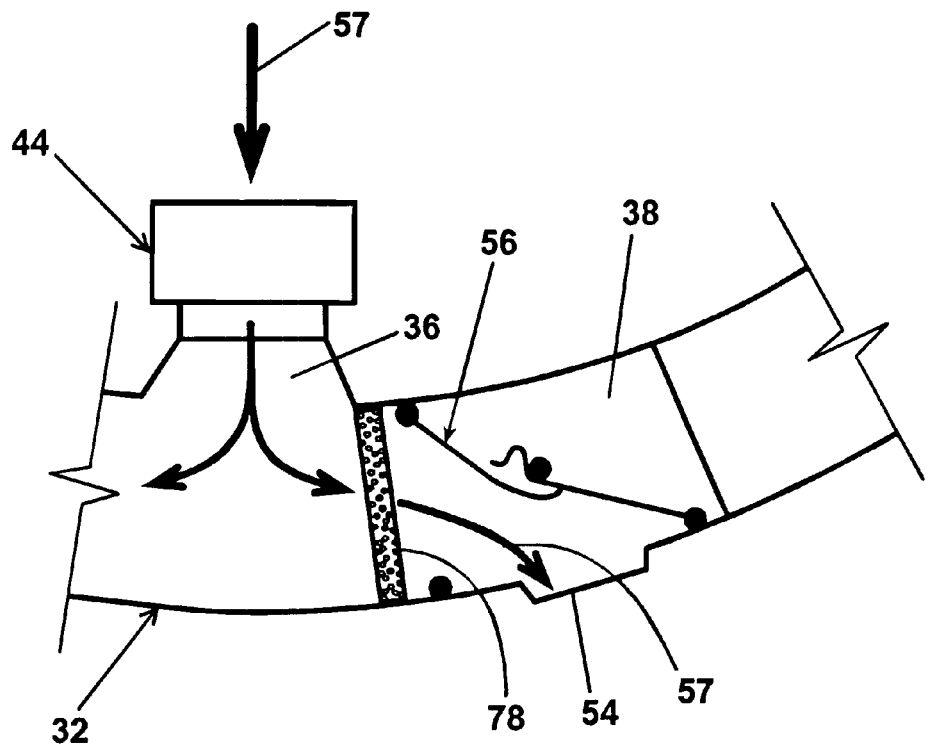
FIG. 11 is a side elevation view of the first valve member of the embodiment of FIG. 1 with a filter.
Figure 12:
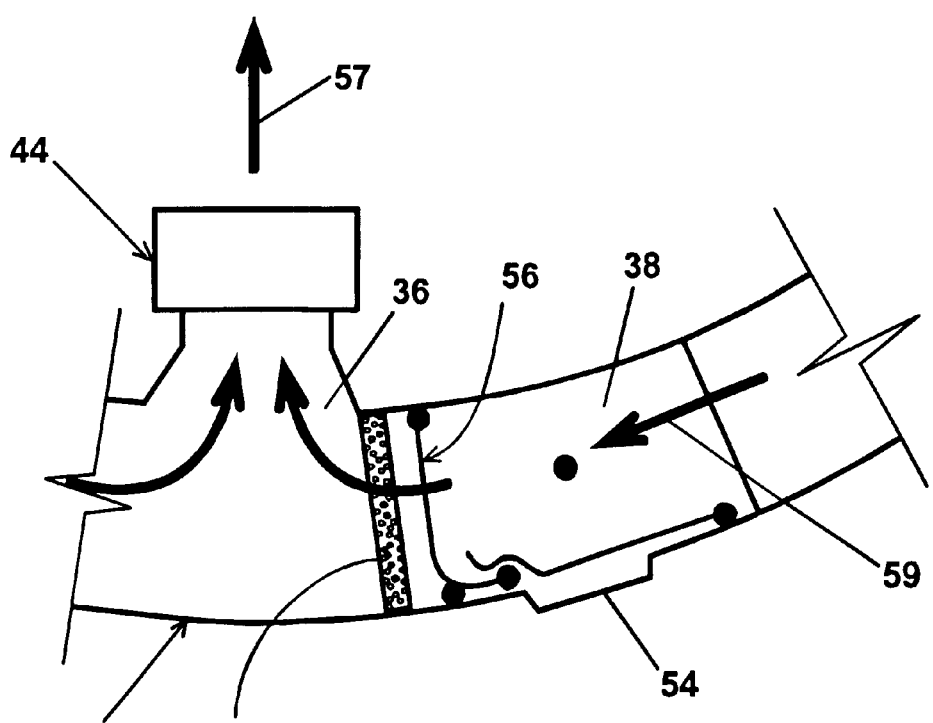
FIG. 12 is a side elevation view of the first valve member of the embodiment of FIG. 1 with a filter.

Referring now to FIGS. 11–12, at least one and preferably two filters 78 may be provided within the body 32. The filters 78 retain heat and/or moisture from the exhale air 57 passing therethrough. When the patient then draws his or her inhale air 59, heat and/or moisture retained by the filters 78 is absorbed into the inhale air 59 thereby providing for increased comfort of the patient 12. The filters 78 may be provided by an air-permeable filter material such as a fabric, plastic, fiber, composite, or other material known by those skilled in the art. The filters 78 may be arranged within the body 32 between the nasal aperture 36 and the exhale aperture 54, outside the body 32 adjacent the exhale aperture 54, or in another position as will be understood by those skilled in the art.

Figure 13:
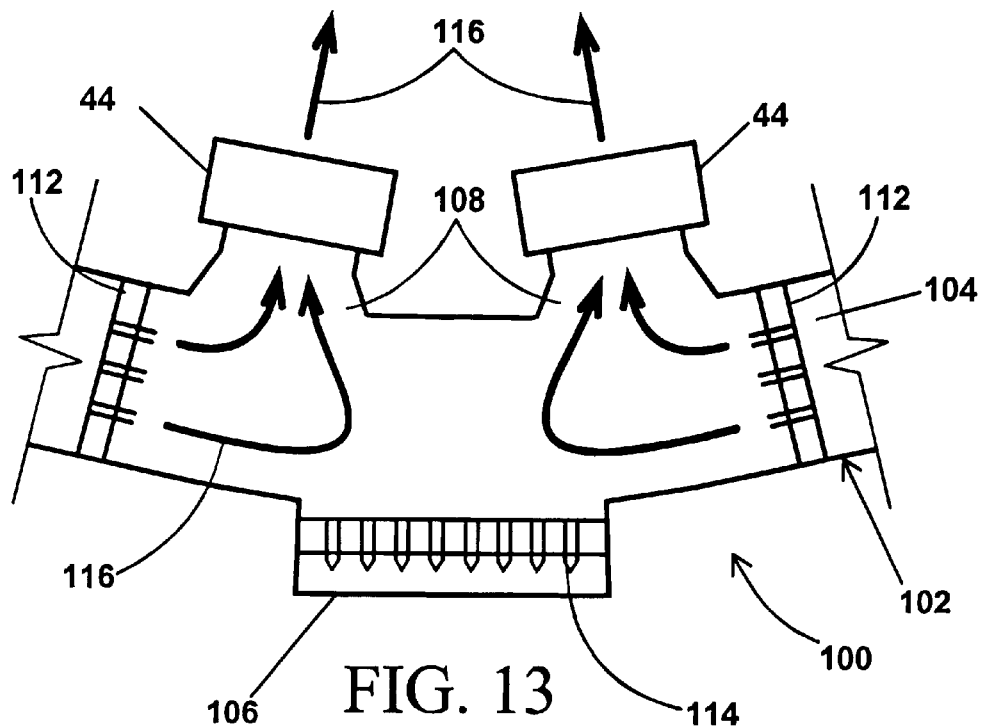
FIG. 13 is a side elevation view of a second embodiment of the present invention during the inspiratory cycle.
Figure 14:
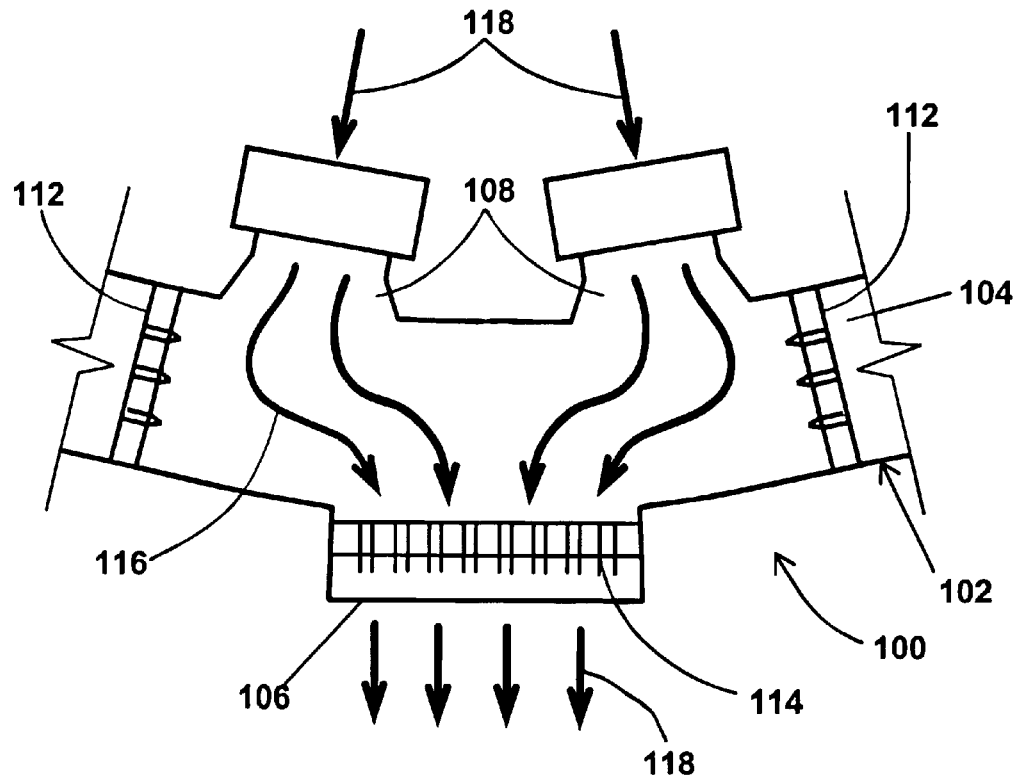
FIG. 14 is a side elevation view of the second embodiment of FIG. 13 during the expiratory cycle.

Referring now to FIGS. 13–14, there is provided a second embodiment 100 of the present invention. Similar to the first embodiment 10 described hereinabove, the second embodiment 100 has a body 102 with at least one and preferably two inhale apertures 104, at least one and alternatively two or more exhale apertures 106, at least one and preferably two nasal apertures 108, and at least one valve assembly 110. Each valve assembly 110 may comprise at least one and preferably two one-way inhale valve membranes 112 and at least one and alternatively two one-way exhale valve membranes 114. The inhale valve membranes 112 may be arranged in the body 102 between one of the nasal apertures 108 and one of the exhale apertures 106 or may be disposed within the inhale aperture 104. The exhale valve membranes 114 may be disposed within the exhale apertures 106. The one-way inhale and exhale membranes 112 and 114 may be provided of a material similar to that of the first valve member 58 of the first embodiment 10. The valve assembly 110 thereby prevents inhalation air 116 from passing through the exhale aperture 106 when the patient inhales and allows exhale air 118 to pass through the exhale aperture 106 when the patient exhales.

In the use of the first and second embodiments 10 and 100 of the present invention, the body 32 is positioned under the nose of the patient 12 with the nasal insert tubes 44 inserted into the patient's nostrils and with the sleeves 46 securing and sealing the body 32 in place. The lengths of interface tubing 22 are positioned over the patient's ears so that the junction 28 is positioned under the patient's chin or behind the patient's back. The mechanical ventilator 18 is operated to supply air to the nasal interface 10 at a positive pressure, thereby forcing air through the feed tubing 14, the interface tubing 22, the interface 10, and into the patient's nostrils and respiratory system to fully sustain the patient's breathing.

When the patient 12 inhales and initiates the inspiratory cycle, he or she typically generates about a negative 1 to 2 centimeters or so of water pressure. A demand valve (not shown) of the ventilator 18 may be triggered by this negative pressure thereby starting a positive flow of air into the interface 10. The patient 12 is thereby able to draw inhalation air 57 through the first valve member 58 in its first position, but not through the exhale aperture 54 as it is then covered by the second valve member 66.

Upon the tidal inhalation airflow 57 volume being delivered through the hollow body 32 and nasal insert tubes 44 and to the patient's lungs, the positive pressure of the inspiratory cycle flow ends. The patient 12 then initiates the expiratory portion of the inhale/exhale cycle. There is not enough back pressure to create static pressure in the body 32, so when the patient 12 begins to exhale air 59 the first valve member 58 is forceably pivoted to its second position, thereby forceably pivoting the second valve member 66 to its second position where exhale air 59 may flow through the exhale aperture 54. The cycle may then repeat itself.

Referring now to FIGS. 15–18, there is provided a third embodiment 200 of the present invention. Similar to the first embodiment 10 described hereinabove, the third embodiment 200 has a hollow body 202 with at least one inhale aperture 204, at least one exhale aperture 206, and at least one and preferably two nasal apertures 208, and at least one nasal insert tube 210 removably coupled to or integrally formed with the body 202 and in fluid communication with each nasal aperture 208. At least one valve assembly 212 may be disposed within the body 202 as may be desired in a given application.

The insert tubes 210 have annular sleeves 214 similar to those of the first embodiment 10 such that each annular sleeve 214 forms a seal with the inner wall of the nostril and additionally exerts a force thereon sufficient to support the weight of the third embodiment interface 200 in place during respiration. In this embodiment, the body 200 is not connected to interface tubing, a mechanical ventilator, or a gas supply, so the body 202 need not have tubing connectors. Instead, the interface 200 provided is a small, lightweight, plug that is held securely in place by the annular sleeves 214. The combined cross-sectional area of the nasal apertures 208 and the combined cross-sectional area of the exhale apertures 206 are each therefore sized to provide a larger cross-sectional area than that of the nostrils so that the patient does not blow the interface 200 out of his or her nose when exhaling.

In the third embodiment 200, there is provided at least one filter 216 disposed within the body 202. The filter 216 may be made of a material capable of retaining dust, allergens, pollen, bacteria, pathogens, and other air-borne particle matter from air passing therethrough. The filters 216 may be provided by an air-permeable filter material such as a thin layer of a treated fabric, plastic, fiber, composite, or other material. For example, the filter 216 may be made of a commercially available material known to be used at the air outlet (where the feed tubing 14 is connected) of some mechanical ventilators 18. When the patient 12 inhales, the undesired airborne matter is screened out of the air by the filter 216 before entering the patient's nostrils thereby providing for increased health and comfort of the patient 12.

Figure 15:
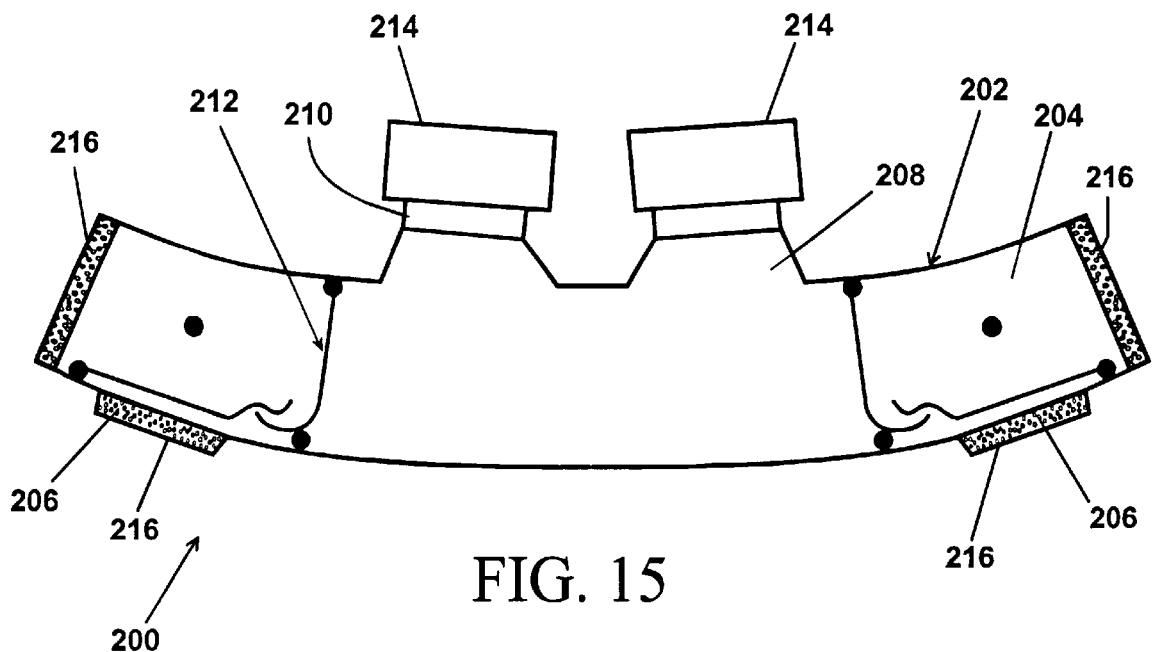
FIG. 15 is a side elevation view of a third embodiment of the present invention.
Figure 16:
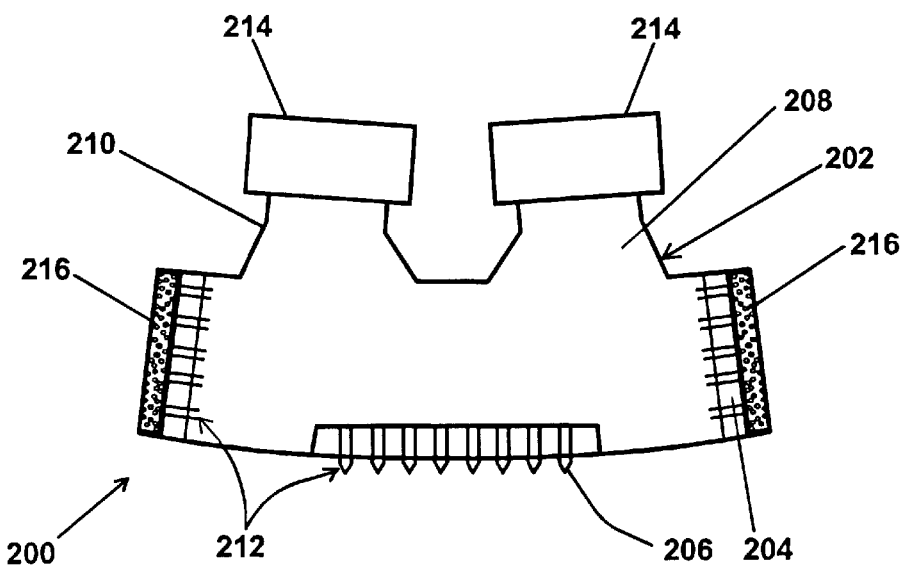
FIG. 16 is a side elevation view of a first alternative third embodiment of the present invention.
Figure 17:
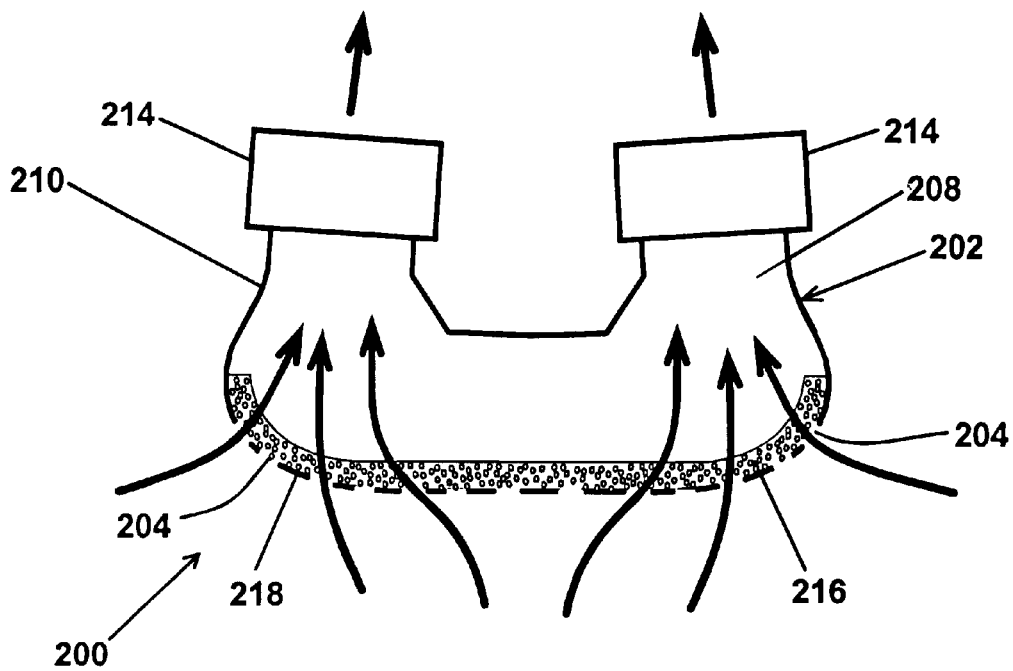
FIG. 17 is a side elevation view of a second alternative third embodiment of the present invention during the inspiratory cycle.
Figure 18:
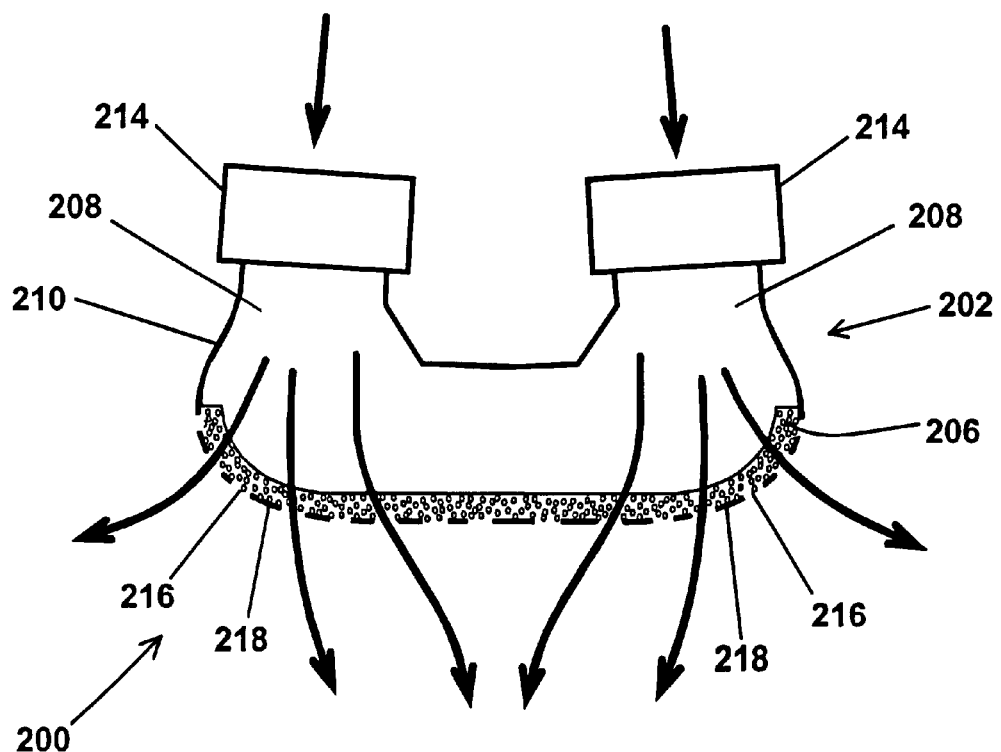
FIG. 18 is a side elevation view of the second alternative third embodiment of FIG. 17 during the expiratory cycle.

The filter or filters 216 may be arranged within the body 202 in various arrangements several of which will now be described. As shown in FIG. 15, the at least one inhale aperture 204 may be provided by two apertures, the at least one exhale aperture 206 may be provided by two apertures, and the valve assembly 212 may be similar to that of the first embodiment 10. In a first alternative third embodiment as shown in FIG. 16, the at least one inhale aperture 204 may be provided by two apertures, the at least one exhale aperture 206 may be provided by a single aperture, the at least one filter 216 may be provided by a filter 216 in fluid communication with each inhale aperture 204 (without a filter at the exhale aperture 206), and the valve assembly 212 may be similar to that of the second embodiment 100. In a second alternative third embodiment as shown in FIGS. 17–18, the at least one inhale aperture 204 and the at least one exhale aperture 206 may be provided by a plurality of apertures spaced across a surface 218 of the body 202, the at least one filter 216 may be provided by one filter 216 in fluid communication with the inhale and exhale apertures 204 and 206 and extending across the surface 218, and the interface 200 may be provided without a valve assembly. The apertures 204 and 206 in the surface 218 may be provided along the length of the body 202 and/or around the perimeter or circumference of the body 202.

In the use of the third embodiment interface 200, the body 202 is inserted into the patient's nostrils before going to sleep, during particularly high pollen count days, if the onset of an allergic reaction is suspected, or at other opportune times as will be understood by those skilled in the art. The interface 200 is portable and may be carried in a patient's pocket so as to be readily available for use as a preventive method of avoiding an asthmatic attack and/or allergic reaction. The patient 12 merely inhales and exhales as normal, with the interface 200 held securely in place by the annular sleeves 214 and the filter 216 screening out from air the allergens, dust, pollen, and/or like undesired airborne particle matter. The interface 200 is easily removed from the nostrils by pulling it out by the body 202.

The interface 200 can be also be provided with a filter 216 that screens pathogens, bacteria, viruses, and other airborne particle material from air. In this arrangement, the interface 200 can be used by doctors, surgeons, nurses, and other attendant medical personnel in operating rooms, dentists offices, clinics, and the like to avoid causing infection and disease in the patient whom they are treating.

Accordingly, there are a number of advantages provided by the present invention. The nasal interface 10 provides the advantage of a positive pressure closed system providing for full ventilation of the patient 12 with oxygen enrichment capabilities typically provided by low pressure oxygen concentrator and cannula tubing systems.

The nasal interface 10 having the nasal insert tube 44 with the annular sleeve 46 provides the advantage of improved patient comfort for use over extended periods.

The nasal interface 10 having the nasal insert tube 44 with the annular sleeve 46 provides the advantage of increased gas delivery efficiency and with minimal or no leakage of gas from the nostrils.

The nasal interface 10 having a valve assembly provides the advantage of decreasing the amount of deadspace that is rebreathed by the patient.

The nasal interface 10 having a filter provides the advantage of filtering the air that is inhaled and/or exhaled for heat, moisture, dust, allergens, pollen, bacteria, viruses, pathogens, and other air-borne particle matter, for use in conjunction with a continuous positive pressure ventilation system or the like or for use as a discrete nasal filtration plug without a forced air supply.

While the invention has been described in connection with certain preferred embodiments, it is not intended to limit the scope of the invention to the particular forms set forth, but, on the contrary, it is intended to cover such alternatives, modifications, and equivalents as may be included within the true spirit and scope of the invention as defined by the appended claims. The terms "a" and "an" as used in the specification and claims herein are intended to include singular and plural quantities. All patents, applications and publications referred to herein are hereby incorporated by reference in their entirety.

What is claimed is:

1. A nasal ventilation interface, comprising:
   a) at least one hollow body having at least one nasal aperture defined therein and at least one inhale aperture defined therein;
   b) at least one nasal insert tube associated with each nasal aperture of said body and capable of being inserted into a nostril of a patient, each nasal insert tube having at least one annular sleeve with a contact surface formed thereon and with a diameter that is greater than a diameter of said nasal insert tube, each annular sleeve contact surface capable of forming a seal with the nostril of the patient;
   c) at least one exhale aperture defined in said body and at least one valve assembly associated with said body, said at least one valve assembly being capable of preventing air from passing through said exhale aperture upon the patient inhaling and allowing air to pass through said exhale aperture upon exhaling;
   d) at least one first valve member having a first end and having a second end pivotally attached to a first inner wall of said body between said nasal aperture and said exhale aperture; and
   e) at least one second valve member having a first end and having a second end pivotally attached to a second inner wall of said body opposite said first inner wall and between said exhale aperture and said inhale aperture, said first valve member second end and said second valve member second end capable of abutting each other.

2. The nasal ventilation interface of claim 1, wherein said first valve member has at least one perforation defined therein with at least one biased closure member associated therewith such that air may pass through said perforation in one direction only, and said second valve member is made of a non-perforated material.

3. The nasal ventilation interface of claim 1, wherein said second valve member may pivot to a first position substantially covering said exhale aperture in response to a force thereon from inhaling air through said inhale aperture and said first valve member may pivot to a first position in response to said pivoting of said second valve member, and said first valve member may pivot to a second position in response to a force from exhaling air through said nasal aperture and said second valve member may pivot to a second position in response to said pivoting of said first valve member.

4. The nasal ventilation interface of claim 3, further comprising at least one first stop arranged within said body wherein said first stop limits said pivoting motion of said first valve member to said first position, and at least one second stop arranged within said body wherein said second stop limits said pivoting motion of said second valve member to said second position.

5. The nasal ventilation interface of claim 3, wherein said first valve member has an angled second end and said second valve member has a yoke formed on said second end thereof that receives said first valve member second end when said first valve member and said second valve member are pivoted to said first positions.

6. The nasal ventilation interface of claim 1, further comprising at least one filter associated with said body.

7. The nasal ventilation interface of claim 6, wherein said filter comprises a material capable of retaining matter selected from the group consisting of heat, moisture, dust, allergens, pollen, bacteria, viruses, and pathogens.

8. A nasal ventilation interface, comprising:
   a) at least one hollow body having at least one nasal aperture defined therein and at least one inhale aperture defined therein;
   b) at least one nasal insert tube associated with each nasal aperture of said body and capable of being inserted into a nostril of a patient, each nasal insert tube having at least one annular sleeve with a contact surface formed thereon and with a diameter that is greater than a diameter of said nasal insert tube, each annular sleeve contact surface capable of forming a seal with the nostril of the patient;
   c) at least one exhale aperture defined in said body; and
   d) at least one valve assembly associated with said body, said at least one valve assembly including at least one one-way inhale valve membrane arranged in said body between said nasal aperture and said exhale aperture or disposed within said inhale aperture and at least one one-way exhale valve membrane disposed within said exhale aperture, said at least one one-way inhale valve membrane and said at least one one-way exhale valve membrane each has at least one perforation defined therein with at least one biased closure member associated therewith such that air may pass through said perforation in one direction only;
   whereby, said at least one valve assembly is capable of preventing air from passing through said exhale aperture upon the patient inhaling and allowing air to pass through said exhale aperture upon exhaling.

9. The nasal ventilation interface of claim 8, further comprising at least one filter associated with said body.

10. The nasal ventilation interface of claim 9, wherein said filter comprises a material capable of retaining matter selected from the group consisting of heat, moisture, dust, allergens, pollen, bacteria, viruses, and pathogens.

* * * * *